United States Patent [19]

Sakashita et al.

[11] Patent Number: 4,920,188

[45] Date of Patent: Apr. 24, 1990

[54] CURABLE COMPOSITIONS

[75] Inventors: Takeshi Sakashita, Iwakuni; Narimichi Honda, Yamaguchi; Masami Arata, Iwakuni, all of Japan

[73] Assignee: Mitsui Petrochemical Industries, Ltd., Tokyo, Japan

[21] Appl. No.: 334,105

[22] PCT Filed: Jul. 1, 1988

[86] PCT No.: PCT/JP88/00661

§ 371 Date: Mar. 3, 1989

§ 102(e) Date: Mar. 3, 1989

[87] PCT Pub. No.: WO89/00170

PCT Pub. Date: Jan. 12, 1989

[30] Foreign Application Priority Data

Jul. 3, 1987 [JP] Japan .................................. 62-166736

[51] Int. Cl.$^5$ ................................................. C08F 4/52
[52] U.S. Cl. .................................... 526/196; 526/197; 526/304
[58] Field of Search ..................... 526/196, 197, 304

[56] References Cited

U.S. PATENT DOCUMENTS

| | | | |
|---|---|---|---|
| 3,894,997 | 7/1975 | Nakaguchi et al. | 526/159 |
| 3,989,882 | 11/1976 | Nakaguchi et al. | 526/197 |
| 4,121,032 | 10/1978 | Nakaguchi et al. | 526/197 |
| 4,385,153 | 5/1983 | Ritter | 526/134 |
| 4,535,070 | 8/1985 | McDaniel et al. | 526/106 |
| 4,639,498 | 1/1987 | Ritter | 526/203 |

Primary Examiner—Morton Foelak
Attorney, Agent, or Firm—Sherman and Shalloway

[57] ABSTRACT

A curable composition is provided, comprising a monofunctional (meth)arcylate monomer, a poly functional (meth)acrylate monomer, a (meth)acrylate monomer containing an acidic group and at least one (meth)acryloyloxyl group in its molecule, a monofunctional (meth)acrylamide monomer, and a trialkylboron and/or a partial oxide thereof. The composition has improved low-temperature curability at approximately room temperature and water-resistant adherence, and excellent adhesiveness to tooth substances including enamel and dentin and dental alloys, and gives no adverse influence of stimulation to dental pulp. Most preferably, the composition is used as a bonding agent for dental composite resins.

2 Claims, No Drawings

CURABLE COMPOSITIONS

TECHNICAL FIELD

This invention relates to an acrylate composition. More particularly, it relates to a curable composition useful for dental bonding agents (adhesives) and the like, which has improved low-temperature curability at room temperature and water-resistant adherence, excellent adhesiveness to tooth substances such as enamel and dentin and dental alloys, and no adverse influence including stimulation for dental pulp.

BACKGROUND ART

A number of bonding agents have been proposed for orthodontic and restorative treatments which typical are catalyzed compositions comprises a radical-polymerizable monomer such as a (meth)acrylate vinyl monomer. For example, Japanese Patent Application Kokai No. 60-44508 proposes a curable composition comprising an acrylate or methacrylate vinyl monomer, an aromatic carboxylic acid or an anhydride thereof containing an acryloyloxyl or methacryloyloxyl group, an amine, and a sulfinic acid or a salt thereof. Japanese Patent Application Kokai No. 53-39331 discloses a bonding agent comprising an acrylate or methacrylate ester which is liquid at room temperature, an amine, a sulfinic acid or a salt thereof, and a peroxide. Nihon Shika Hoken (Japanese Dental and Hygienic Journal), 28, 270 (1985) reports a bonding agent comprising methyl methacrylate, 4-META, and tributylboran (TBB).

However, conventional adhesives and curable compositions have problems that they have to be treated by etchants such as phosphoric acid and citric acid in order to obtain improved adherence to dental substances, and that it is difficult to obtain sufficient adherence to dentin particularly if an etching treatment is not carried out to dentin at all, and that an opening in dentin tube is caused by the etching treatment resulting in stimulation to dental pulp.

Therefore, the above-mentioned problems can be solved by the present invention. An object of the present invention is to provide a curable composition having improved curability at room temperature and water-resistant adherence. Another object of the present invention is to provide a curable composition having improved adherence to tooth substances such as enamel and dentin and dental alloys, particularly dentin. A further object of the present invention is to provide a curable composition which can be used as a dental adhesive to bond composite resins for tooth restoration without any adverse influence including stimulation of dental pulp.

DISCLOSURE OF THE INVENTION

According to the present invention, there is provided a curable composition comprising (A) a monofunctional (meth)acrylate monomer, (B) a polyfunctional (meth)acrylate monomer, (C) a (meth)acrylate monomer containing an acidic group and at least one acryloyloxyl or methacryloyloxyl group in its molecule, (D) a monofunctional (meth)acrylamide monomer of the general formula (I):

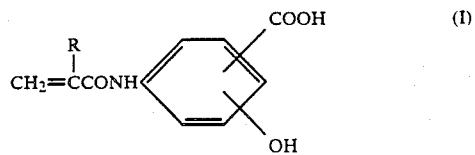

wherein R is H or CH$_3$, and (E) a trialkylboron and/or a partial oxide thereof.

The present invention is hereinafter discribed in detail.

The monofunctional (meth)acrylate monomer (A) used in the curable composition of the present invention may contain in its molecule a functional group other than an acidic group. Examples of the monofunctional (meth)acrylate monomer include (meth)acrylates containing a hydrocarbon group such as methyl (meth)acrylate, ethyl (meth)acrylate, butyl (meth)acrylate, hexyl (meth)acrylate, 2-ethylhexyl (meth)acrylate, dddecyl (meth)acrylate, lauryl (meth)acrylate, cyclohexyl (meth)acrylate, benzyl (meth)acrylate, and isobornyl (meth)acrylate; (meth)acrylates containing a hydroxyl group such as 2-hydroxyethyl (meth)acrylate and 2-hydroxypropyl (meth)acrylate; (meth)acrylates containing an ethylene glycol unit such as ethylene glycol monomethyl ether (meth)acrylate, ethylene glycol monoethyl ether (meth)acrylate, ethylene glycol monododecyl ether (meth)acrylate, diethylene glycol monomethyl ether (meth)crylate, polyethylene glycol monomethyl ether (meth)acrylate, and polyethylene glycol monoethyl ether (meth)acrylate; (meth)acrylates containing a fluorine-substituted group such as trifluoroethyl (meth)acrylate, and perfluorooctyl (meth)acrylate; silane (meth)acrylates such as γ-(meth)acryloyloxypropyltrimethoxysilane, and γ-(meth)acryloyloxypropyltri(trimethylsiloxy)silane; and tetrahydrofurfuryl (meth)acrylate. They may be used alone or in admixture of two or more.

Preferred are alkyl (meth)acrylates such as methyl acrylate and methacrylate, ethyl (meth)acrylate, hexyl (meth)acrylate, and dodecyl (meth)acrylate, and hydroxylcontaining (meth)acrylates such as 2-hydroxyethyl (meth)acrylate, and 2-hydroxypropyl (meth)acrylate. Most preferably, methyl methacrylate, n-hexyl methacrylate, 2-hydroxyethyl methacrylate and 2-hydroxypropyl methacrylate monomers and a mixture thereof are used.

Examples of the polyfunctional acrylate or methacrylate monomer (B) used in the curable composition include poly(meth)acrylates of alkane polyols such as ethylene glycol di(meth)acrylate, propylene glycol di(meth)acrylate, butylene glycol di(meth)acrylate, neopentyl glycol di(meth)acrylate, hexylene glycol di(meth)acrylate, trimethylolpropane tri(meth)acrylate, glycerin tri(meth)acrylate, and pentaerythritol tetra(meth)acrylate; and poly(meth)acrylates of (poly)oxyalkane polyols such as diethylene glycol di(meth)acrylate, dipropylene glycol di(meth)acrylate, triethylene glycol di(meth)acrylate, tetraethylene glycol di(meth)acrylate, dibutylene glycol di(meth)acrylate, and dipentaerythritol hexa(meth)acrylate; epoxy (meth)acrylates of the general formula (II):

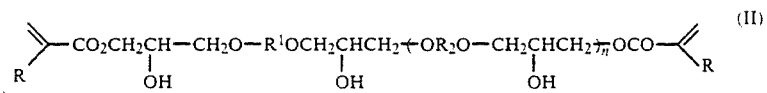 (II)

wherein R is H or CH₃,
n is 0 or a positive integer, and
R¹ is —(CH₂)₂—, —(CH₂)₄—,

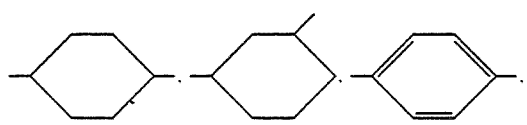

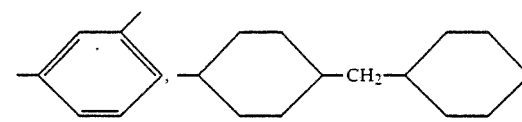

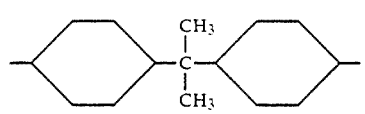

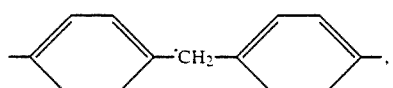

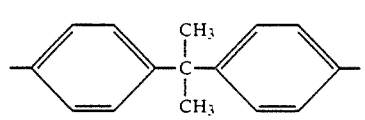

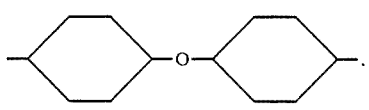

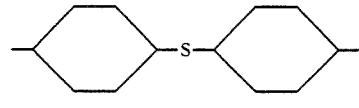

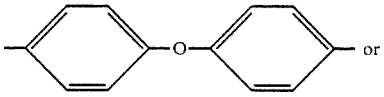 or

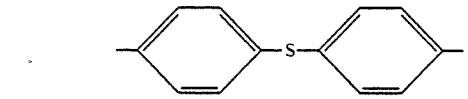

cycloaliphatic or aromatic di(meth)acrylates of the general formula (III):

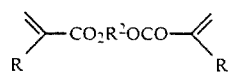 (III)

wherein R is H or CH₃, and

R² is 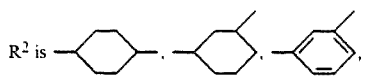,

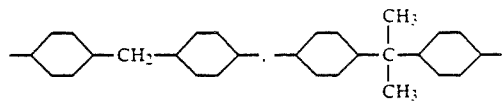

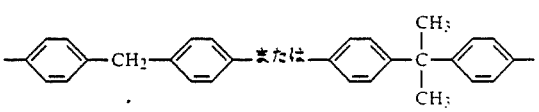

cycloaliphatic di(meth)acrylates of the general formula (IV):

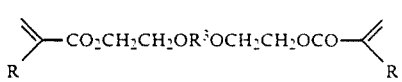 (IV)

wherein R is H or CH₃, and

R³ is 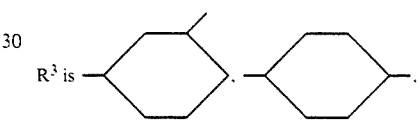

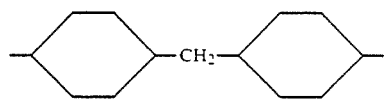

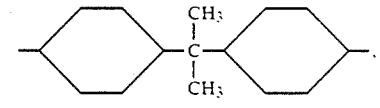,

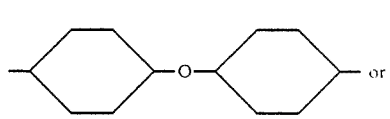 or

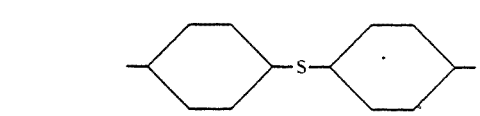

polyfunctional acrylates and methacrylates containing at least one urethane bond in their molecule. An example of the polyfunctional (meth)acrylates is an adduct of 1 mol of diisocyanate and 2 mol of a hydroxy groupcontaining (meth)acrylates such as 2-hydroxyethyl (meth)acrylates.

The diisocyanates may be used aliphatic, cycloaliphatic or aromatic diisocyanate. Examples of the diisocyanates include hexamethylene diisocyanate, lysindiisocyanate, 2,2(4),4-trimethylhexamethylenediisocyanate, dicyclohexyldimethylmethane-P,P'-diisocyanate, isophorondiisocyanate, trilendiisocyanate, xylilenediisocyanate, diphenylmethanediisocyanate, and naphthalenediisocyanate. Further examples of the diisocyanate include

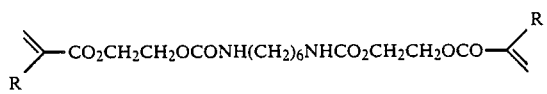
wherein R is H or $CH_3$,
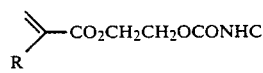
wherein R is H or $CH_3$,
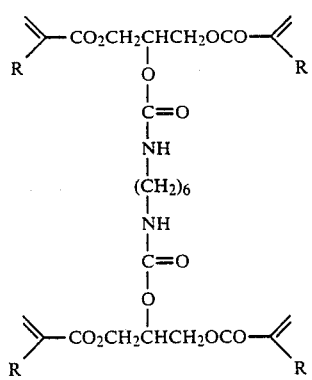
wherein R is H or $CH_3$,
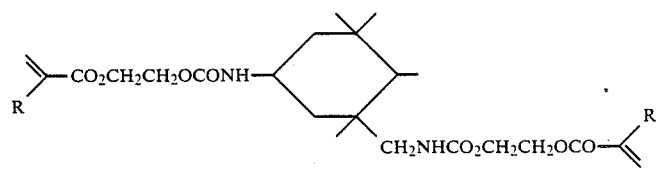
wherein R is H or $CH_3$,
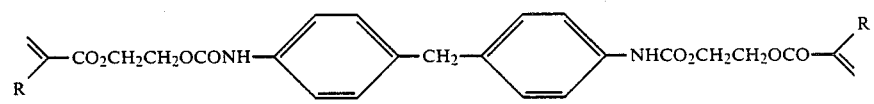
wherein R is H or $CH_3$,
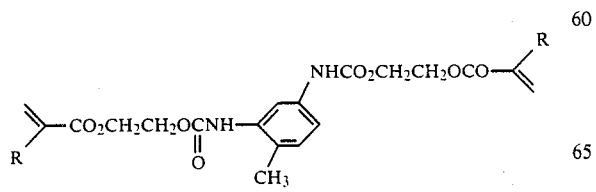
wherein R is H or $CH_3$,
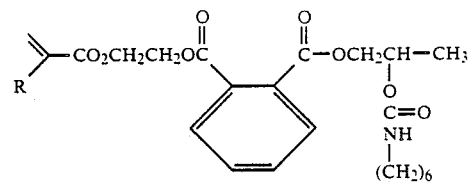
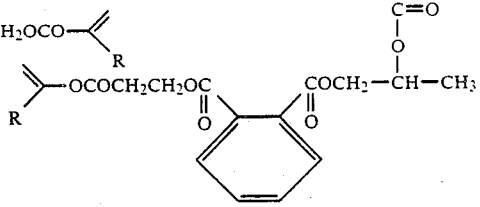
wherein R is H or $CH_3$, and
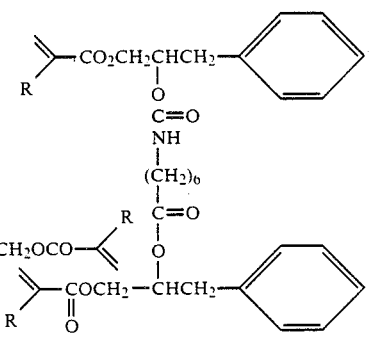
wherein R is H or $CH_3$.
Other examples of monomers (B) include the polyfunctional (meth)acrylates of the general formula (V):

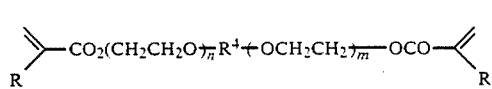

wherein R is H or CH$_3$, R$^4$ is a divalent aromatic residue

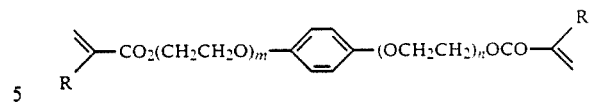

wherein R is H or CH$_3$, and m+n=2 to 20,

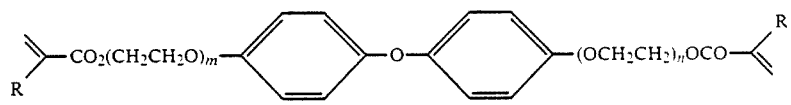

which has at least one aromatic ring and may have an oxygen or sulfur atom in tis molecule, and n and m are positive integers. Examples of the polyfunctional (meth)acrylates of the general formula (V) include wherein R is H or CH$_3$, and m+n=2 to 20,

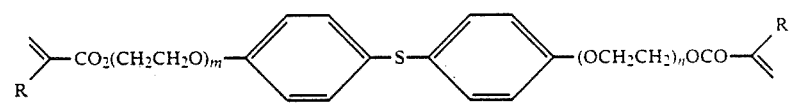

wherein R is H or CH$_3$, and m+n=2 to 20.

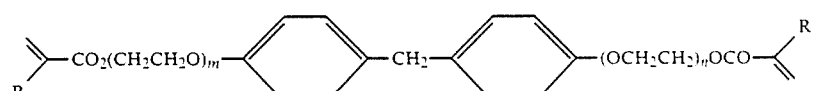

wherein R is H or CH$_3$, and m+n=2 to 20,

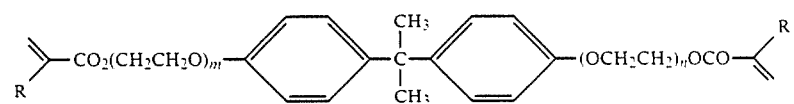

wherein R is H or CH$_3$, and m+n=2 to 20.

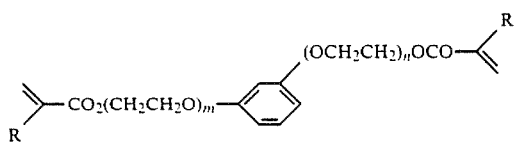

wherein R is H or CH$_3$, and m+n=2 to 20,

Among these polyfunctional (meth)acrylate monomers, preferred are the monomers of alkane polyol poly(methacrylate. (poly)oxyalkanepolyol poly(meth)acrylate, epoxy(meth)acrylate, aliphatic or cycloaliphatic (meth)acrylate containing at least one urethane bond in its molecule, and (poly)oxyalkanepolyol poly(meth)acrylate having aromatic rings. Most preferred monomers are ethyleneglycol di(meth)acrylate, neopentylglycol (meth)acrylate, diethyleneglycol di(meth)acrylate, triethylene glycol di(meth)acrylate,

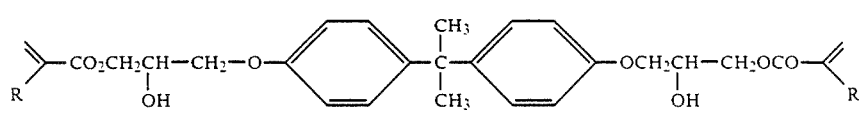

wherein R is H or CH$_3$,

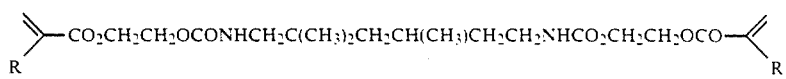

wherein R is H or CH$_3$,

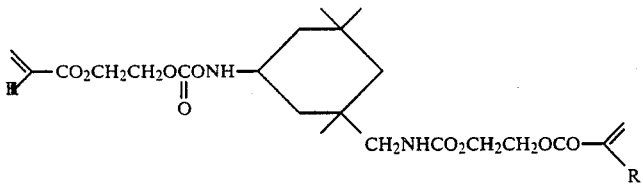

wherein R is H or CH₃,

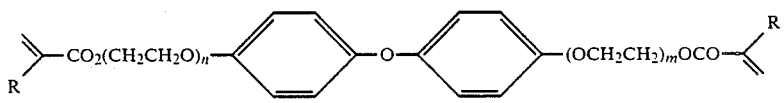

wherein R is H or CH₃, and m+n=2 to 10, and

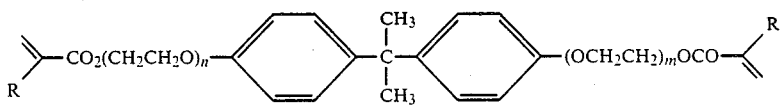

wherein R is H or CH₃, and m+n=2 to 10.

They may be used alone or in admixture of two or more.

In the curable composition according to the present invention, the (meth)acrylate monomer containing an acidic group and at least one (meth)acryloyloxyl group in its molecule (C) includes (C₁) aromatic polycarboxylic acids having at leaqst one (meth)acryloyloxyl group per molecule or anhydrides thereof and (C₂) partial esters of phosphoric or sulfonic acid having at least one (meth)acyloyloxyl group per molecule, such as monoesters and diesters of phosphoric acid and mixtures thereof, and monoesters of sulfonic acid.

Examples of the aromatic polycarboxylic acid having at least one (meth)acryloyloxyl group per molecure (C₁) are (meth)acryloyloxyl-containing aromatic polycarboxylic acids or anhydrides thereof having the structure wherein an alkane polyol has at least two hydroxyl groups per molecule and may contain an oxygen atom, at least one of its hydroxyl groups forms an ester with (meth)acrylic acid and at least one of its hydroxyl groups forms an ester with one carboxyl group of an aromatic polycarboxylic acid having at least three carboxyl groups.

The preferred aromatic polycarboxylic acids containing at least three carboxyl groups are aromatic polycarboxylic acids in which at least two of the carboxyl groups are attached to the adjoining carbon atom on the aromatic nucleus. Examples of the aromatic polycarboxylic acids are hemimellitic acid, trimellitic acid, prehnitic acid, mellophanic acid, and pyromellitic acid.

The (meth)acryloyloxyl-containing aromatic polycarboxylic acids or anhydrides thereof include 4-(meth)acryloyloxymethoxycarbonylphthalic acid or an anhydride thereof, 4-(meth)acryloyloxyethoxy-carbonylphthalic acid or an anhydride thereof, 4-(meth)acryloyloxybutoxycarbonylphthalic acid or an anhydride thereof,

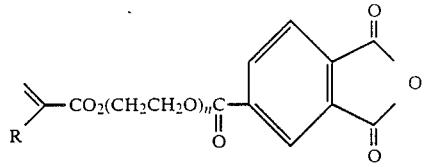

wherein R is H or CH₃, and n is an integer of from 6 to 12,

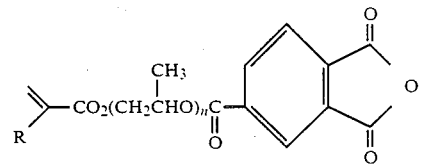

wherein R is H or CH₃, and n is an integer of from 2 to 50, wherein R is H or CH₃, and n is an integer of from 1 to 50, 4-[2-hydroxy-3-(meth)acryloyoxypropoxycarbonyl]phthalic acid or an acid anhydride thereof, 2,3-bis(3,4-dicarboxybenzoyloxy)propylmethacrylate 2,3-bis(3,4-dicarboxybenzoyloxy)propylmethacrylate or an acid anhydride thereof, and 2-(3,4-dicarboxylbenzoyloxy)-1,3-dimethacryloyoxypropane or an acid anhydride thereof.

The partial esters of phosphoric or sulfonic acid having at least one (meth)acryloyloxyl group per molecule (C₂) include monoesters and diesters of sulfonic acid, for example, 2-(meth)acryloyloxyehtylphenyl acid phosphate, bis-[2-(meth)acryloyl-oxyethyl]acid phosphate, bis[3-(meth)acryloxypropyl]acid phosphate, 2-(meth)acryloyloxyethylphenyl phosphonate,

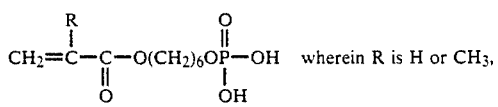 wherein R is H or CH$_3$,

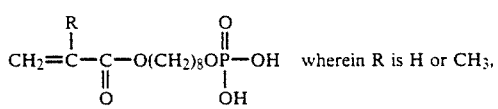 wherein R is H or CH$_3$,

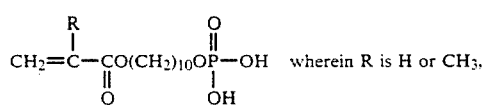 wherein R is H or CH$_3$,

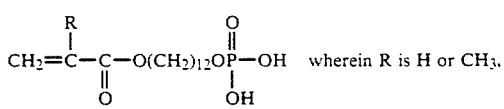 wherein R is H or CH$_3$,

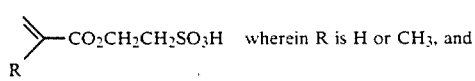 wherein R is H or CH$_3$, and

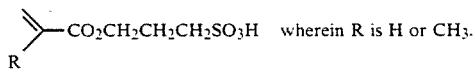 wherein R is H or CH$_3$.

Among these (meth)acrylate monomers containing an acidic group and at least one (meth)acryloyloxyl group in its molecule (C), preferred are aromatic polycarboxylic acids having at least one (meth)acryloyloxyl group per molecule or acid anhydrides thereof (C$_1$). More preferred are 4-(meth)acryloyloxy-ethoxycarbonylphthalic acid or its acid anhydride. Most preferably, 4-(meth)acryloyloxyethoxycarbonylphthalic acid anhydride is used because of improved adherence to tooth and water-durability.

In the curable composition of the present invention, a monofunctional (meth)acrylate monomer (D) of the general formula (I) is used. Examples of the monofunctional (meth)acrylamide monomer are 3-(meth)acryloylaminosalicylic acid, 4-(meth)acryloyl-aminosalicylic acid, 5-(meth)acryloylaminosalicylic acid, 3-hydroxy-2-(meth)acryloylaminobenzoic acid, 3-hydroxy-4-(meth)acryloylaminobenzoic acid, 3-hydroxy-5-(meth)acryloylaminobenzoic acid, 3-hydroxy-6-(meth)acryloylaminobenzoic acid, 4-hydroxy-2-(meth)acrylaminobenzoic acid, and 4-hydroxy-3-(meth)acryloylaminobenzoic acid. They may be used alone or in admixture of two or more. Among these monofunctional (meth)acrylate monomer, preferred are 3-(meth)acryloylaminosalicylic acid, 4-(meth)acryloylaminosalicylic acid, and 5-(meth)acryloylaminosalicylic acid. Most preferably, 4-(meth)acryloylaminosalicylic acid and 5-(meth)acryloylaminosalicylic acid are used alone or in admixture.

The curable composition of the present invention further comprises (E) a trialkylboron or its partial oxide. Examples of the trialkylboron include triethylboron, tripropylboron, triisopropylboron, tri-n-butylboron, tri-n-amylboron, triisoamylboron, tri-sec-amylboron, and partial oxides of these trialkylborons in which the trialkylborons are partially oxidized. Preferably, tri-n-butylboron and its partial oxides are used.

In the curable composition of the present invention, the proportion of the monofunctional (meth)acrylate monomer (A) and the polyfunctional (meth)acrylate monomer (B) blended therein is not particularly limited. Better results are obtained when the curable composition generally contains 5 to 95% by weight of the monofunctional (meth)acrylate monomer (A) and 95 to 5% by weight of the polyfunctional (meth)acrylate monomer (B), preferably 10 to 95% by weight of the monofunctional (meth)acrylate monomer (A) and 90 to 5% by weight of the polyfunctional (meth)acrylate monomer (B), and most preferably 25 to 90% by weight of the monofunctional (meth)acrylate monomer (A) and 75 to 10% by weight of the polyfunctional (meth)acrylate monomer (B), because adhesiveness to dentin and water-durability exhibit improved, particularly adhesiveness and water-durability to non-etched dentin.

In the curable composition of the present invention, the proportion of the acidic group-containing (meth)acrylate monomer (C) blended therein generally ranges from 1 to 50 parts by weight, preferably from 3 to 30 parts by weight, most preferably from 5 to 15 parts by weight per 100 parts by weight of the total of the monofunctional (meth)acrylate monomer (A) and the polyfunctional (meth)acrylate monomer (B) blended therein.

In the curable composition of the present invention, the proportion of the monofunctional (meth)acrylamide monomer (D) of the general formula (I) blended therein generally ranges from 0.1 to 50 parts by weight, preferably from 0.3 to 30 parts by weight, most preferably from 1 to 15 parts by weight per 100 parts by weight of the total of the monofunctional (meth)acrylate monomer (A) and the polyfunctional (meth)acrylate monomer (B) blended therein.

In the curable composition of the present invention, the proportion of the trialkylboron or its partial oxide (E) blended therein generally ranges from 2 to 100 parts by weight, preferably from 5 to 70 parts by weight, most preferably from 5 to 50 parts by weight per 100 parts by weight of the total of the monofunctional (meth)acrylate monomer (A), the polyfunctional (meth)acrylate monomer (B), the acidic group-containing (meth)acrylate monomer (C) and the monofunctional (meth)acrylamide monomer (D) of the general formula (I) blended therein.

The curable composition of the present invention may contain any desired additives in addition to the abovementioned essential components, for example, other polymerizable monomers, organic solvents, powder inorganic fillers, organic polymers, and polymerization retarders.

Examples of the other polymerizable monomers include vinyl halogenides such as vinyl chloride and vinyl bromide; vinyl esters such as vinyl acetate and vinyl propyonate; vinyl ethers such as methylvinyl ether, ethylvinyl ether and isobutylvinyl ether; alkenyl benzenes such as styrene, vinyltoluene, α-methylstyrene, chloromethylstyrene and stilbene.

Examples of the organic solvents include ethyl alcohol, acetone, ethyl acetate, diethyl ether, tetrahydrofuran, N,N-dimethyl acetoamide, N-methyl pyrorydone and dimethyl sulfoxide.

Examples of the powder inorganic fillers include kaolin, talc, clay, calcium carbonate, silica, silicaalumina, titanium oxide, calcium phosphate, ground glass, and ground quartz.

Examples of the organic polymers include wax, ethylene-vinyl acetate copolymers, and polymethylacrylate.

polymetylmethacrylate, and copolymers thereof. These fillers or additives may be blended in any desired proportion.

The curable composition of the present invention is prepared by mixing each of the above-mentioned components (A), (B), (C), (D) and (E), and may also contain other optional components. In this case, the proportion of each of the above-mentioned components (A), (B), (C), (D) and (E) may be adjusted as desired. In order to get good procedure at the use, a part of them is dissolved in an organic solvent, mixed the solution with the other components and applied it to dental surface before curing leading to polymerized-curing the compositions, or each of the components is separately applied to the surface leading to polymerized-curing the compositions. Since the trialkylboron or its partial oxide (E) starts polymerization reaction with the (meth)acrylate monomers (A), (B) and (C) and the (meth)acrylamide monomer (D) within several seconds to several ten minutes after their mixing, the trialkylboron (E) is kept separate from the above-mentioned components (A), (B), (C) and (D) and mixed with the latter components immediately before use.

BEST MODE FOR CARRYING OUT THE INVENTION

Examples of the present invention are presented below by way of illustration and not by way of limitation.

Evaluation of the curable composition of the present invention is described below together with examples of preparing the photo-curable composite resin used in Examples and Comparative Examples. The abbreviations used herein have the following meanings.

MMA: methyl methacrylate,
HMA: n-hexyl methacrylate,
HEMA: 2-hydroxyethyl methacrylate,
HEPA: 2-hydroxypropyl methacrylate,
DPEMA:

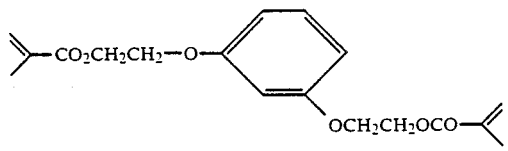

UDMA:

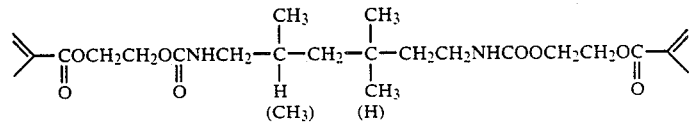

4-META:

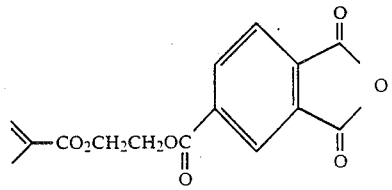

4-MET:

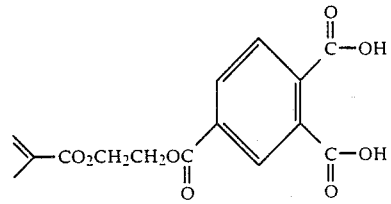

4-MASA:

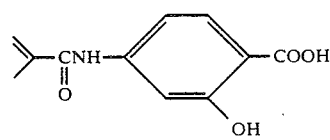

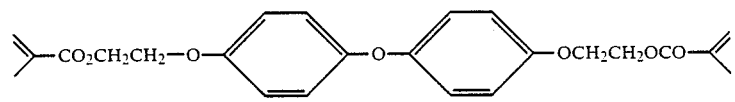

2.6E:

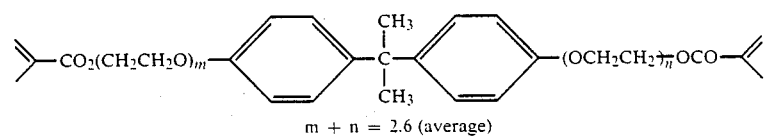

RDMA:

5-MASA:

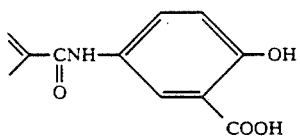

TBB-0: partial oxide of tri-n-butylboron
BPO: benzoyl peroxide
DEPT: diethanol p-toluidine
PTSNa: sodium p-toluenesulfonate
HQME: hydroquinone monomethylether 1. Evaluation of adhesiveness The enamel or dentin surface of a bovine anterior tooth on its labial face was fully polished with #600 emery paper to smoothen the surface. The enamel was etched for 30 seconds with an aqueous solution of 65% by weight of phosphoric acid. After thorough rinsing, the etched surface was dried by air blowing. A piece of adhesive tape of about 13 mm by 13 mm having a circular opening of 5 mm in diameter was attached to the etched surface. The bonding agent described in Examples or Comparative Examples was applied to the surface in the opening, and lightly air blown. A cylindrical mold of polytetrafluoroethylene having a diameter of 5 mm and a height of 2 mm was mated with the circular opening in the adhesive tape and filled with the photopolymerizable composite resin described later. The composite resin filling was covered on the surface with a cellophane sheet, and exposed for 30 seconds to visible light from a visible light source, Translux (manufactured by Kulzer) to cure the composite resin. An acryl resin bar was bonded to the surface of the cured composite resin with an adhesive, Super-Bond C&B (manufactured by Sun Medical K.K.) to form a bond test specimen. The specimen was allowed to stand for 30 minutes at room temperature, immersed for 24 hours in water at a temperature of 37° C., allowed to stand for 10 minutes in air at a temperature of 23° C., and then subjected to a tensile test at a temperature of 23° C. and a pulling rate of 2 mm/min to measure a bonding force. After the bond test, the rupture surface exhibited bovine tooth rupture, cohesive rupture of the composite resin, or interfacial rupture between the composite resin and the dentin.

2. Preparation of photo-curable composite resin

A composition was prepared by milling 7.5 grams of triethylene glycol dimethacrylate, 7.5 grams of 1,3-bis-(methacryloxyethoxy)benzene, 15 grams of an adduct of 1 mol of 2,2,4-trimethylhexamethylenediamine diisocyanate and 2 mol of 2-hydroxyethyl methacrylate, 40 grams of a composite filler synthesized by the following method, 30 grams of finely divided silica (RM-50, Nihon Aerosil K.K.), and 4 mg of hydroquinone monomethyl ether in a two-roll mill at 35° C. A photo-curable composite resin was prepared by combining 10 grams of the composition with 45 mg of camphorquinone and 45 mg of 4-diethylaminobenzoic acid and fully admixing the mixture with a spatula.

3. Preparation of composite filler

A solution of 0.1 gram benzoyl peroxide in 10 grams of trimethylolpropane trimethacrylate was placed in an agate mortar. Finely divided silica (Aerosil R972, Nihon Aerosil K.K., average particle size of 16 m$\mu$) was added to the solution in increments while mixing. As silica was added, the viscosity of the mixture gradually increased. When the mixture became somewhat crumby, it was transferred to a small-size rubber roll mill. Finely divided silica was further added until a total amount of 9.5 grams was reached. The resulting paste was removed from the mill and het cured for 10 minutes in a press at a mold temperature of 110° C. under a pressure of 150 to 200 kg/cm$^2$. The cured product was ground in a ball mill so as to pass a 230 mesh screen, obtaining 18.0 grams of a composite filler. The filler had an average particle size of 11 $\mu$m.

EXAMPLE 1

A monomer mixed liquid (A) was prepared by mixing 6.0 grams of methyl methacrylate (MMA), 3.0 grams of 1,3-bis(methacryloxy)benzene (RDMA), 1.0 gram of 4-methacryoxy ethoxy carboxylic phthalic acid anhydride (4-META), 0.1 gram of 4-methacryloyl aminosalicylic acid (4-MASA), and 2.0 milligrams of hydroquinone monomethyl ether (HQME) at room temperature. A curable composition was prepared by mixing 2 parts by weight of the monomer liquid (A) with 1 part by weight of a partial oxide of tri-n-butylboron (TBB-0, Sun Medical K.K.). The composition was applied to the tooth surface with a small brush. A bond test specimen was then prepared by the aforesaid method. The results are shown in Table 1.

EXAMPLES 2–11 AND COMPARATIVE EXAMPLES 1–4

Bond test specimens were prepared by repeating the procedure of Example 1 except that the monomers used in Example 1 were replaced by other monomers shown in Table 1 in the amounts reported in Table 1. The results are shown in Table 1.

COMPARATIVE EXAMPLE 5

A monomer liquid (A) was prepared by mixing 3.0 grams of MMA, 3.0 grams of HEMA, 3.0 grams of 2,6E, 1.0 gram of 4-HETA, 0.2 grams of 5-MASA, 0.1 gram of BPO and 2.0 milligrams of HQME at room temperature. Separately, a liquid (B) was prepared by dissolving 0.05 grams of DEPT and 0.2 grams of PTSNa in 9.75 grams of 99% ethyl alcohol. The curable composition was prepared by mixing equal parts by weigh of (A) and (B) at room temperature. The composition was applied to the tooth surface with a small brush. A bond test specimen was prepared by the aforesaid method. The results are shown in Table.

TABLE 1

|  | Example 1 | Example 2 | Example 3 | Example 4 | Example 5 | Example 6 |
|---|---|---|---|---|---|---|
| Curable composition |  |  |  |  |  |  |
| Monofunctional (meth)acrylate monomer (A) |  |  |  |  |  |  |
| type | MMA | MMA | MMA | MMA | MMA/HEMA | MMA/HEMA |
| amount, weight ratio | — | — | — | — | 90/10 | 50/50 |
| Polyfunctional (meth)acrylate monomer (B) |  |  |  |  |  |  |
| type | RDMA | 2,6E | DPEMA | UDMA | DPEMA | UDMA |
| amount, B/(A + B) wt % | 33 | 33 | 33 | 33 | 33 | 33 |
| Acidic group-containing (meth)acrylate |  |  |  |  |  |  |

TABLE 1-continued

| monomer (C) | | | | | | |
|---|---|---|---|---|---|---|
| type | 4-META | 4-MET | 4-META | 4-MET | 4-META | 4-META |
| amount, C/(A + B) wt % | 11 | 11 | 11 | 11 | 11 | 11 |
| Monofunctional (meth)acrylamide monomer (D) | | | | | | |
| type | 4-MASA | 4-MASA | 5-MASA | 5-MASA | 4-MASA | 4-MASA |
| amount, D/(A + B) wt % | 1.1 | 1.1 | 1.1 | 1.1 | 2.2 | 5.5 |
| Partial oxide of trialkylboron (E) | | | | | | |
| type | TBB.O | TBB.O | TBB.O | TBB.O | TBB.O | TBB.O |
| amount, E/(A + B + C + D) wt % | 50 | 50 | 50 | 50 | 50 | 50 |
| Adhesiveness | | | | | | |
| Enamel, after water immersion @ 37° C., 1 day, kg/cm$^2$ | 197 | 215 | 190 | 193 | 205 | 193 |
| Dentin, after water immersion @ 37° C., 1 day, kg/cm$^2$ | 68 | 63 | 82 | 77 | 70 | 67 |

| | Example 7 | Example 8 | Example 9 | Example 10 | Example 11 |
|---|---|---|---|---|---|
| Curable composition | | | | | |
| Monofunctional (meth)acrylate monomer (A) | | | | | |
| type | MMA/HEMA | MMA/HEMA | HEMA | HMA | MMA/HEMA |
| amount, weight ratio | 80/20 | 50/50 | — | — | 20/80 |
| Polyfunctional (meth)acrylate monomer (B) | | | | | |
| type | 2.6E | RDMA | 2.6E | 2.6E | 2.6E |
| amount, B/(A + B) wt % | 33 | 33 | 50 | 50 | 50 |
| Acidic group-containing (meth)acrylate monomer (C) | | | | | |
| type | 4-META | 4-META | 4-META | 4-META | 4-MET |
| amount, C/(A + B) wt % | 11 | 11 | 10 | 10 | 10 |
| Monofunctional (meth)acrylamide monomer (D) | | | | | |
| type | 5-MASA | 5-MASA | 4-MASA | 5-MASA | 5-MASA |
| amount, D/(A + B) wt % | 2.2 | 5.5 | 5 | 1 | 3 |
| Partial oxide of trialkylboron (E) | | | | | |
| type | TBB.O | TBB.O | TBB.O | TBB.O | TBB.O |
| amount, E/(A + B + C + D) wt % | 50 | 50 | 50 | 33 | 25 |
| Adhesiveness | | | | | |
| Enamel, after water immersion @ 37° C., 1 day, kg/cm$^2$ | 220 | 211 | 178 | 195 | 182 |
| Dentin, after water immersion @ 37° C., 1 day, kg/cm$^2$ | 93 | 83 | 71 | 90 | 90 |

| | Comparative Example 1 | Comparative Example 2 | Comparative Example 3 | Comparative Example 4 | Comparative Example 5 |
|---|---|---|---|---|---|
| Curable composition | | | | | |
| Monofunctional (meth)acrylate monomer (A) | | | | | |
| type | — | MMA | MMA/HEMA | MMA/HEMA | MMA/HEMA |
| amount, weight ratio | — | — | 80/20 | 80/20 | 50/50 |
| Polyfunctional (meth)acrylate monomer (B) | | | | | |
| type | 2.6E | — | 2.6E | 2.6E | 2.6E |
| amount, B/(A + B) wt % | 100 | 0 | 33 | 33 | 33 |
| Acidic group-containing (meth)acrylate monomer (C) | | | | | |
| type | 4-META | 4-META | — | 4-META | 4-META |
| amount, C/(A + B) wt % | 11 | 11 | 0 | 11 | 11 |
| Monofunctional (meth)acrylaide monomer (D) | | | | | |
| type | 5-MASA | 5-MASA | 5-MASA | — | 5-MASA |
| amount, D/(A + B) wt % | 1.1 | 1.1 | 2 | 0 | 2.2 |
| Partial oxide of trialkylboron (E) | | | | | |
| type | TBB.O | TBB.O | TBB.O | TBB.O | (BPO/DEPT/PTSNa) |
| amount, E/(A + B + C + D) wt % | 50 | 50 | 50 | 50 | 1/0.5/2 |
| Adhesiveness | | | | | |
| Enamel, after water immersion @ 37° C., 1 day, kg/cm$^2$ | 131 | 175 | 103 | 215 | 135 |
| Dentin, after water immersion @ 37° C., 1 day, kg/cm$^2$ | 27 | 23 | 27 | 33 | 12 |

EXAMPLE 12

A solution (a), dissolving 1.0 gram of 4-methacryloylaminosalicylic acid (4-MASA) in 19 grams of ethyl alcohol was applied to the tooth surface. The ethyl alcohol was almost evaporated by lightly air blowing. Separately, a monomer liquid was prepared by mixing 6.0 grams of methyl methacrylate (MMA), 3.0 grams of 1,3-bis(methacryloxy ethoxy) benzene (RDMA), 1.0 gram of 4-methacryloxy ethoxy carboxylic phthalic acid anhydride (4-META) and 2.0 milligrams of hydroquinone monomethyl ether (HQME) at room temperature. A liquid (b) was prepared by mixing 2 parts by weight of the monomer liquid with 1 part by weight of a partial oxide of tri-n-butylboron (TBB-0, Sun Medical K.K.). The liquid (b) of the equal amount of the solution (a) was applied to the tooth surface. A bond test specimen was prepared by the aforesaid method. The results are shown in Table 2.

EXAMPLES 13–17

Bond test specimens were prepared by repeating the procedure of Example 12 except that the monomers used in Example 12 were replaced by other monomers shown in Table 2 in the amounts shown in Table 2. The results are shown in Table 2.

|  | Comparative Example 12 | Comparative Example 13 | Comparative Example 14 | Comparative Example 15 | Comparative Example 16 | Comparative Example 17 |
|---|---|---|---|---|---|---|
| Curable composition | | | | | | |
| Monofunctional (meth)acrylate monomer (A) | | | | | | |
| type | MMA | MMA/HEMA | MMA/HEMA | MMA/HEMA | MMA/HEMA | MMA |
| amount, weight ratio | — | 85/15 | 50/50 | 85/15 | 85/15 | — |
| Polyfunctional (meth)acrylate monomer (B) | | | | | | |
| type | RDMA | 2.6E | DPEMA | 2.6E | UDMA | RDMA |
| amount, B/(A + B) wt % | 33 | 33 | 33 | 33 | 50 | 30 |
| Acidic group-containing (meth)acrylate monomer (C) | | | | | | |
| type | 4-META | 4-META | 4-MET | 4-META | 4-META | 4-META |
| amount, C/(A + B) wt % | 11 | 11 | 11 | 11 | 10 | 5 |
| Monofunctional (meth)acrylamide monomer (D) | | | | | | |
| type | 4-MASA | 5-MASA | 5-MASA | 5-MASA | 4-MASA | 4-MASA |
| amount, D/(A + B) wt % | 5.5 | 5.5 | 5.5 | 1.1 | 5 | 5 |
| Partial oxide of trialkylboron (E) | | | | | | |
| type | TBB.O | TBB.O | TBB.O | TBB.O | TBB.O | TBB.O |
| amount, E/(A + B + C + D) wt % | 50 | 50 | 50 | 50 | 25 | 50 |
| Adhesiveness | | | | | | |
| Enamel, after water immersion @ 37° C., 1 day, kg/cm² | 213 | 210 | 185 | 203 | 218 | 177 |
| Dentin, after water immersion @ 37° C., 1 day, kg/cm² | 80 | 125 | 97 | 118 | 107 | 79 |

The bond tests showed that the compositions of the Examples had superior water-resistant adherence to enamel and dentin, on the contrary, the compositions of the Comparative Examples which lack at least one of the components (A), (B), (C), (D) and (E) of the present invention had inferior water-resistant adherence to enamel and/or dentin.

INDUSTRIAL APPLICABILITY

The composition of the present invention comprises the above-mentioned (A), (B), (C), (D) and (E). The composition has improved low-temperature curability at room temperature and water-resistant adherence, and exhibits excellent adhesiveness to tooth substances including enamel and dentin and dental alloys, and gives no adverse influence including stimulation of dental pulp.

Therefore, the composition can be used as a bonding agent not only for dental composite resins and rigid resins, but also for various composite resins used in precision working other than dental applications. Most preferably, the composition is used as a bonding agent for dental composite resins.

We claim:

1. A curable composition comprising,
   (A) a monofunctional (meth)acrylate monomer,
   (B) a polyfunctional (meth)acrylate monomer,
   (C) a (meth)acrylate monomer containing an acidic group and at least one (meth)acryloyloxyl group in its molecule,
   (D) a monofunctional (meth)acrylamide monomer of the general formula (I):

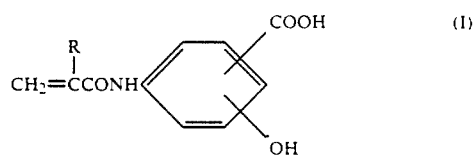

wherein R is H or CH$_3$, and
   (E) a trialkylboron and/or a partial oxide thereof.

2. The curable composition of claim 1 wherein (A) comprises 5 to 95% by weight and (B) comprises 95 to 5% by weight based on the total weight of (A) and (B), (C) comprises 1 to 50 parts by weight per 100 parts by weight of the total of (A) and (B), (D) comprises 0.1 to 50 parts by weight per 100 parts by weight of the total of (A) and (B), and (E) comprises 2 to 100 parts by weight per 100 parts by weight of the total of (A), (B), (C) and (D).

* * * * *